United States Patent
Niebling et al.

(10) Patent No.: US 11,548,006 B2
(45) Date of Patent: Jan. 10, 2023

(54) APPARATUS AND METHOD OF COLLECTING A SAMPLE FOR DETERMINATION OF 1, 4 DIOXANE IN DRINKING WATER

(71) Applicant: SUFFOLK COUNTY WATER AUTHORITY, Oakdale, NY (US)

(72) Inventors: Christopher H. Niebling, Oakdale, NY (US); Thomas E. Schneider, Oakdale, NY (US); Francisco Vilas Boas, Oakdale, NY (US)

( * ) Notice: Subject to any disclaimer, the term of this patent is extended or adjusted under 35 U.S.C. 154(b) by 57 days.

(21) Appl. No.: 17/331,071

(22) Filed: May 26, 2021

(65) Prior Publication Data

US 2021/0291188 A1    Sep. 23, 2021

Related U.S. Application Data

(62) Division of application No. 16/185,046, filed on Nov. 9, 2018, now Pat. No. 11,045,809.

(51) Int. Cl.
  *G01N 33/18* (2006.01)
  *G01N 1/10* (2006.01)
  *B01L 3/00* (2006.01)

(52) U.S. Cl.
  CPC .......... *B01L 3/52* (2013.01); *G01N 1/10* (2013.01); *G01N 33/1826* (2013.01); *B01L 2200/16* (2013.01)

(58) Field of Classification Search
  CPC ....... B01L 2200/026; B01L 2200/0605; B01L 2200/16; B01L 2400/065; B01L 3/52; B01L 3/523; G01N 1/10; G01N 1/12; G01N 1/38; G01N 33/18; G01N 33/1826; Y10T 436/142222; Y10T 436/20; Y10T 436/25; Y10T 436/2575
  USPC .......... 436/93, 127, 174, 180; 422/501, 521
  See application file for complete search history.

(56) References Cited

U.S. PATENT DOCUMENTS

| | | | |
|---|---|---|---|
| 6,033,384 A | * | 3/2000 | Py .......................... A61F 9/0026 222/207 |
| 10,578,634 B2 | | 3/2020 | Lehtonen et al. |
| 11,045,809 B2 | * | 6/2021 | Niebling ................. B01L 3/523 |
| 2012/0241045 A1 | | 9/2012 | Aouad |
| 2015/0367304 A1 | * | 12/2015 | Aouad .................... B01F 35/13 366/141 |
| 2022/0236297 A1 | * | 7/2022 | Lehtonen .................. B65B 3/26 |

* cited by examiner

*Primary Examiner* — Maureen Wallenhorst
(74) *Attorney, Agent, or Firm* — Heslin Rothenberg Farley & Mesiti P.C.

(57) ABSTRACT

A reagent dispenser includes a housing. A container of microbial inhibitor is disposed within the housing. A dispensing system is disposed within the housing and operable to dispense the microbial inhibitor from the container. The dispensing system is calibrated to dispense a calibrated weight per water sample of the microbial inhibitor, such that a ratio of the calibrated weight per water sample to inner volume of a sample bottle substantially equals a predetermined concentration of microbial inhibitor per liter of water determined to acidify water to a pH of 4 or less.

10 Claims, 8 Drawing Sheets

FIG. 1A

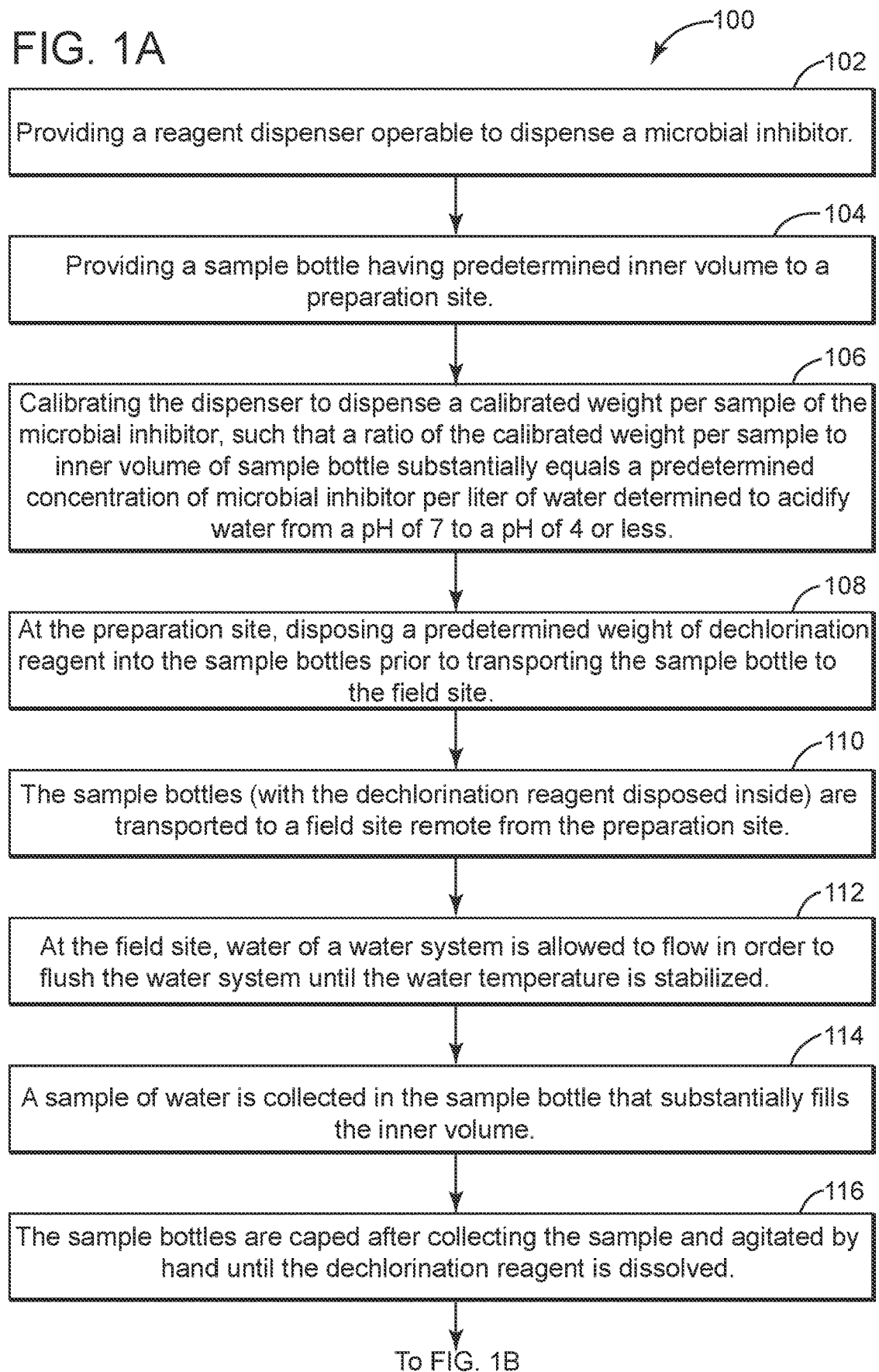

102 — Providing a reagent dispenser operable to dispense a microbial inhibitor.

104 — Providing a sample bottle having predetermined inner volume to a preparation site.

106 — Calibrating the dispenser to dispense a calibrated weight per sample of the microbial inhibitor, such that a ratio of the calibrated weight per sample to inner volume of sample bottle substantially equals a predetermined concentration of microbial inhibitor per liter of water determined to acidify water from a pH of 7 to a pH of 4 or less.

108 — At the preparation site, disposing a predetermined weight of dechlorination reagent into the sample bottles prior to transporting the sample bottle to the field site.

110 — The sample bottles (with the dechlorination reagent disposed inside) are transported to a field site remote from the preparation site.

112 — At the field site, water of a water system is allowed to flow in order to flush the water system until the water temperature is stabilized.

114 — A sample of water is collected in the sample bottle that substantially fills the inner volume.

116 — The sample bottles are caped after collecting the sample and agitated by hand until the dechlorination reagent is dissolved.

To FIG. 1B

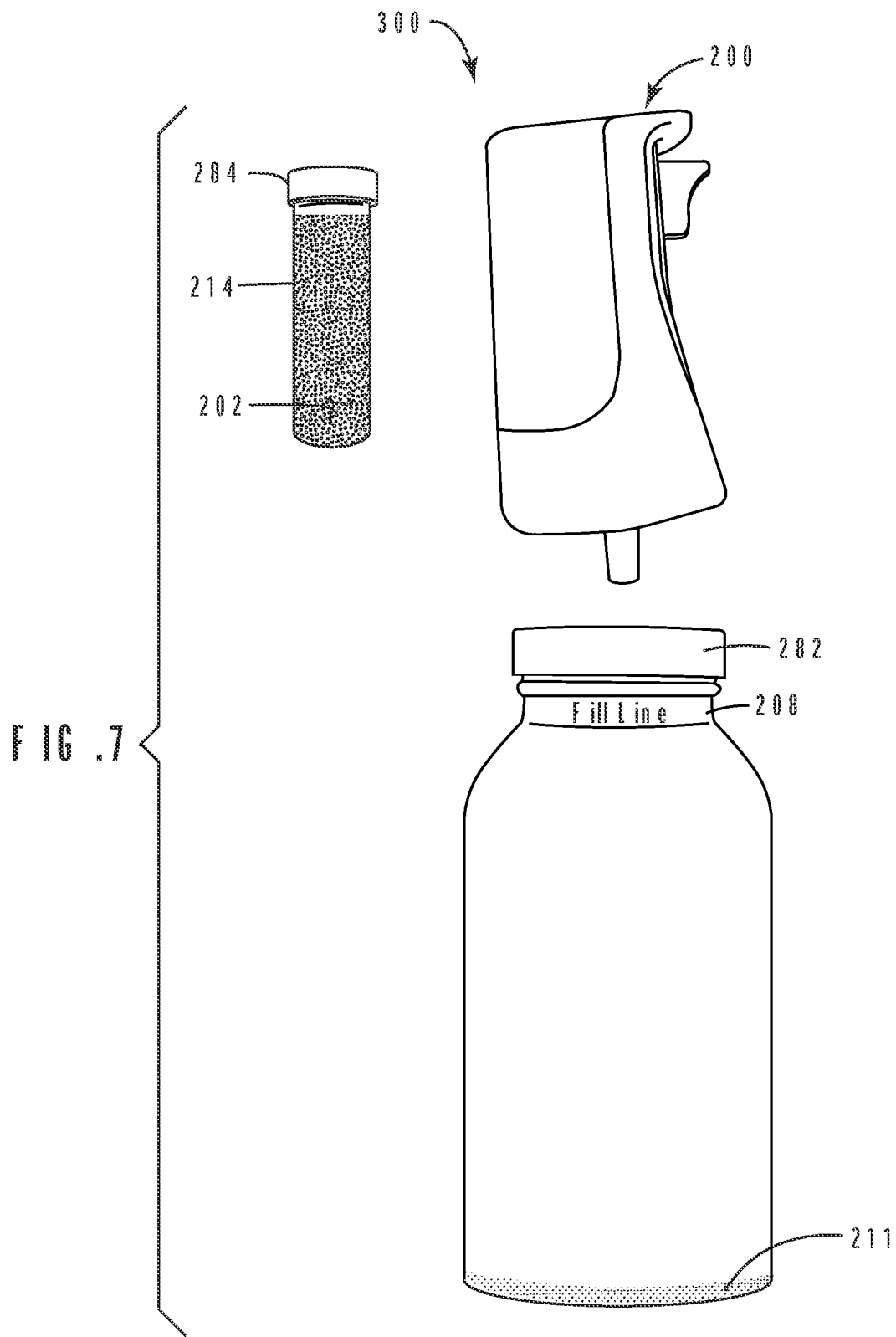

APPARATUS AND METHOD OF COLLECTING A SAMPLE FOR DETERMINATION OF 1, 4 DIOXANE IN DRINKING WATER

CROSS-REFERENCE TO RELATED APPLICATIONS

This application claims priority to U.S. patent application Ser. No. 16/185,046, now U.S. Pat. No. 11,045,809 entitled "AN APPARATUS AND METHOD OF COLLECTING A SAMPLE FOR DETERMINATION OF 1, 4-DIOXANE IN DRINKING WATER" and filed on Nov. 9, 2018, which is incorporated herein by reference in its entirety.

BACKGROUND 1,4-dioxane has been classified by the U.S. Environmental Protection Agency (the EPA) as an emerging contaminant. It is a clear liquid that is often used as a solvent stabilizer in the manufacture of other chemicals. It is a by-product that is present in many goods, including paint strippers, dyes, greases, antifreeze and aircraft deicing fluids. 1, 4-dioxane is also found in some consumer products such as deodorants, shampoos and cosmetics.

1, 4-dioxane is a likely human carcinogen and has been found in groundwater at sites throughout the United States. Once it makes its way into sources of drinking water, 1, 4-dioxane tends to stay there, as it does not break down easily. Further, it is completely miscible in water, highly mobile and very resistant to microbial degradation.

Accordingly, there is an increasing need to reliably test for 1, 4-dioxane in drinking water sources. Additionally, there is an increasing need to be able to reliably obtain and prepare drinking water samples from field sites and to transport them back to a suitable laboratory for 1, 4-dioxane testing.

Suffolk County Water Authority (Oakdale, N.Y.) is a public benefit corporation and is specifically created to supply potable water to residents of Suffolk County, New York. There are many other districts or entities that perform the same function in communities throughout the United States. Many such water providers have an increasing need to reliably sample and test ground water produced at numerous sites throughout their distribution system for 1, 4, dioxane. Moreover, many environmental laboratories, that often service these water providers, are also increasingly required to receive samples of water taken in the field and test them for 1, 4-dioxane.

One example of an emerging de facto standard for sampling and testing ground water for 1, 4-dioxane is the EPA Method 522 (herein Method 522). Method 522 is titled:

"Determination of 1, 4-Dioxane in Drinking Water by Solid Phase Extraction (SPE) and Gas Chromatography/Mass Spectrometry (GC/MS) with Selected Ion Monitoring (SIM),"

and was first published in September of 2008.

Method 522 requires that a microbial inhibitor be added in precise amounts to a drinking water sample immediately after the sample has been collected. The microbial inhibitor is utilized to substantially reduce microbial growth in the sample during transport and storage of the sample, prior to testing. However, Method 522 is silent as to how the microbial inhibitor may be added.

For Suffolk County Water Authority and other large water purveyors, that may be required to take several thousand drinking water samples per year, reliably and accurately adding such a microbial inhibitor to each sample at each field site can be problematic. This is because it is expensive to carry laboratory measuring equipment to every field site that is remotely located from the laboratory where the testing is to take place. Additionally, such laboratory measuring equipment is more prone to damage or wear in the field. Further, the probability for human error increases dramatically when the measuring equipment is used in the field.

Accordingly, there is a need for a method that can reliably and accurately preserve drinking water samples collected in the field and store them for future testing in a laboratory. Additionally, there is a need for equipment that can be utilized in such a method that is not prone to breaking down and can reduce the probability of human error.

BRIEF DESCRIPTION

The present disclosure offers advantages and alternatives over the prior art by providing a method of collecting a sample for determination of 1, 4-dioxane in drinking water utilizing a reagent dispenser to preserve the drinking water sample. The method reduces the probability of human error. The reagent dispenser dispenses a microbial inhibitor into the collected sample of drinking water reliably and accurately without the need for expensive and fragile laboratory equipment.

A method of collecting a sample for determination of 1, 4-dioxane in drinking water in accordance with one or more aspects of the present disclosure includes providing a reagent dispenser operable to dispense a microbial inhibitor. A sample bottle having a predetermined inner volume is provided to a preparation site. The dispenser is calibrated to dispense a calibrated weight per water sample of the microbial inhibitor, such that a ratio of the calibrated weight per water sample to inner volume of the sample bottle substantially equals a predetermined concentration of microbial inhibitor per liter of water determined to acidify water to a pH of 4 or less. The sample bottle is transported to a field site, the field site being remote from the preparation site. A sample of water is collected in the sample bottle at the field site that substantially fills the inner volume. The dispenser is operated to substantially dispense the calibrated weight per water sample of microbial inhibitor into the sample of water collected in the sample bottle.

A reagent dispenser in accordance with one or more aspects of the present disclosure includes a housing. A container of microbial inhibitor is disposed within the housing. A dispensing system is disposed within the housing and operable to dispense the microbial inhibitor from the container. The dispensing system is calibrated to dispense a calibrated weight per water sample of the microbial inhibitor, such that a ratio of the calibrated weight per water sample to inner volume of a sample bottle substantially equals a predetermined concentration of microbial inhibitor per liter of water determined to acidify water to a pH of 4 or less.

A kit in accordance with one or more aspects of the present disclosure includes a supply of microbial inhibitor and a reagent dispenser. The reagent dispenser is operable to dispense the microbial inhibitor. The dispenser is calibrated to dispense a calibrated weight per water sample of the microbial inhibitor, such that a ratio of the calibrated weight per water sample to inner volume of a sample bottle substantially equals a predetermined concentration of microbial inhibitor per liter of water determined to acidify water to a pH of 4 or less.

DRAWINGS

The invention will be more fully understood from the following detailed description taken in conjunction with the accompanying drawings, in which:

FIG. 7 depicts an example of a perspective view of a dispenser kit for collecting a sample for determination of 1, 4-dioxane in drinking water according to aspects described herein.

DETAILED DESCRIPTION

Certain exemplary embodiments will now be described to provide an overall understanding of the principles of the structure, function, manufacture and use of the methods, systems, and devices disclosed herein. One or more examples of these embodiments are illustrated in the accompanying drawing. Those skilled in the art will understand that the methods, systems, and devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The terms "substantially", "approximately", "about", "relatively," or other such similar terms that may be used throughout this disclosure, including the claims, are used to describe and account for small fluctuations, such as due to variations in processing. For example, they can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%. Also, by way of example, such terms may only include positive fluctuations, such as up to plus 5% or up to plus 10%.

Figure 1:
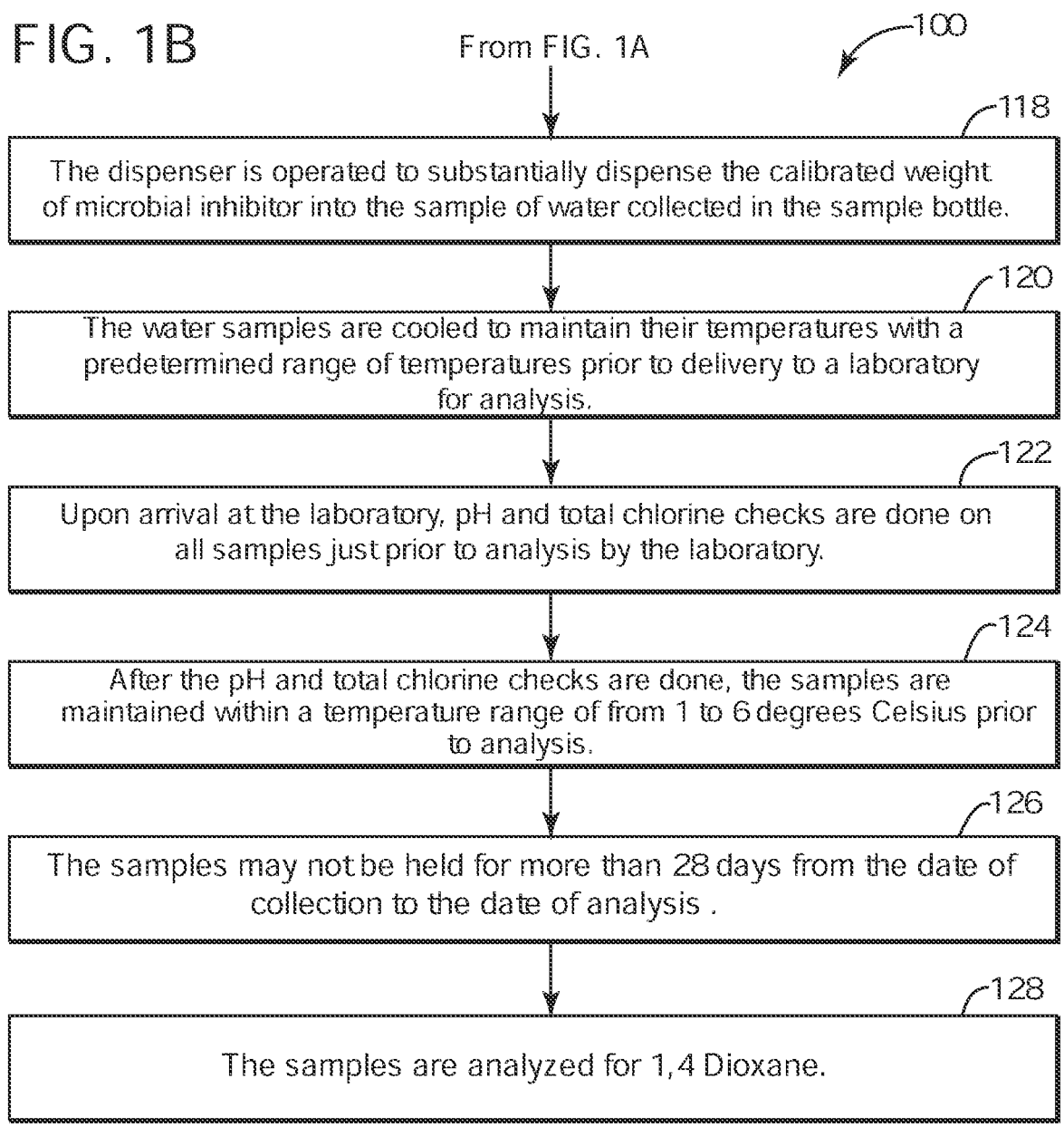
FIG. 1A depicts a first portion of an example of a method of collecting a sample for determination of 1, 4-dioxane in drinking water according to aspects described herein.
FIG. 1B depicts a second portion of the example FIG. 1A of a method of collecting the sample for determination of 1, 4-dioxane in drinking water according to aspects described herein.

Referring to FIG. 1, an example of a method 100 of collecting a sample for determination of 1, 4-dioxane in drinking water in accordance with aspects described herein is depicted. As will be discussed in greater detail herein, the method 100 enables a precise amount of a microbial inhibitor 202 to be added reliably and accurately to drinking water samples 206 immediately after the samples have been collected. Additionally, the method 100 does not require the use of expensive and fragile laboratory measuring equipment. Further the method 100 reduces the probability of human error when utilized by hundreds of personnel to collect thousands of samples from hundreds of field locations (or sites).

The method 100 begins at 102 of FIG. 1, wherein a reagent dispenser 200 (seen in FIG. 2) is provided. The reagent dispenser 200 is operable to dispense a specific microbial inhibitor 202 (seen in FIG. 2). The microbial inhibitor 202 may be sodium bisulfate and may be in the form of a dry granulated salt in order to meet the requirements of EPA test method 522.

Though sodium bisulfate is used as an example of a microbial inhibitor, one skilled in the art would recognize that other microbial inhibitors may also be used. Some examples of potential alternative microbial inhibitors include: copper sulfate, diazolidinyl urea, potassium dihydrogen citrate or the like.

The method proceeds to 104 of FIG. 1, wherein one or more sample bottles 208 (seen in FIG. 2), having a predetermined inner volume 209, are also provided and delivered to a preparation site. The sample bottles 208 are operable to collect drinking water samples 206 at field sites that are remotely located from the preparation site.

The sample bottles 208 may be amber colored to prevent direct sun light from penetrating a collected water sample 206. The predetermined inner volume 209 of the sample bottle 208 may be any known volume that is sized to be manually portable. However, the inner volume 209 is often an integer multiple of 250 milliliters (ml), such as 250 ml, 500 ml, 750 ml or 1.0 liters.

The method proceeds to 106 of FIG. 1, wherein the reagent dispenser 200 is calibrated to dispense a calibrated weight per water sample 205 (seen in FIG. 2) of the microbial inhibitor 202, such that a ratio of the calibrated weight per water sample 205 to inner volume 209 of the sample bottle 208 substantially equals a predetermined concentration of microbial inhibitor per liter of water determined to acidify water to a pH of 4 or less.

The calibrated weight per water sample 205 may be any weight of microbial inhibitor 202 that, when mixed with a sample of drinking water 206, may acidify the water to a pH of 4 or less. For example, if sodium bisulfate is utilized as the microbial inhibitor 202, it has been determined that a concentration of substantially 1.0 gram (g) of microbial inhibitor per liter (L) of water will, in most cases, lower the pH of the water from a value of 7 to a value of 4 or less.

To illustrate by way of a specific example, the microbial inhibitor 202 may be sodium bisulfate and the sample bottles 208 may have an inner volume 209 of 250 milliliters (mL). As such, the reagent dispenser 200 may be calibrated to dispense a calibrated weight per water sample 205 of 250 milligrams (mg) in order to attain the desired concentration of 1.0 g/L.

The dispenser 200 does not have to dispense the calibrated weight per water sample 205 in one application. Again, by way of the same specific example wherein the microbial inhibitor 202 is sodium bisulfate and the sample bottles 208 have an inner volume 209 of 250 ml, the reagent dispenser 200 may be sized to dispense a discrete calibrated weight per application 204 (seen in FIG. 2) of 125 mg of sodium bisulfate with each application. As will be explained in greater detail herein, each application of the dispenser 200 may be applied by fully depressing (i.e., pumping) a triggering mechanism 218 (seen in FIG. 3) associated with the dispenser 200. Accordingly for the specific example used herein, it would take two pumps of the dispenser's triggering mechanism 218 to dispense the calibrated weight per water sample 205 of 250 mg of sodium bisulfate into the 250 ml sample bottle. This is because each pump of the triggering mechanism 218 would dispense a calibrated weight per application 204 of 125 mg of sodium bisulfate.

Moreover, if the calibrated weight per application 205 of the sodium bisulfate for any given size sample bottle 208 was within plus 10% of an integer multiple of 125 milligrams, it would take that integer number of pumps to dispense the calibrated weight per application 205 from the dispenser 200 of this example. More specifically, for a 500 ml sample bottle, it would take 4 pumps of the dispenser 200, dispensing a calibrated weight per application 204 of 125 mg of sodium bisulfate per pump, to provide the required calibrated weight per water sample 205. Further, for a 750 ml sample bottle it would take 6 pumps of the dispenser's triggering mechanism 202 and for a 1 liter sample bottle it would take 8 pumps.

The method proceeds to 108 of FIG. 1, wherein, at the preparation site, a predetermined weight of dechlorination reagent 211 (seen in FIGS. 2 and 7) is disposed into the sample bottle 208 prior to transporting the sample bottle to the field site. The preparation site may be any site where the controlled deposit of dechlorination reagent 211 into the sample bottles 208 is practical. For example, the preparation site may be a laboratory or a shipping and receiving area of a facility of a water purveyor.

The dechlorination reagent 211 is added to the sample bottles 208 such that a ratio of the predetermined weight of dechlorination reagent 211 to the inner volume 209 substantially equals a predetermined concentration of dechlorination reagent per liter of water determined to reduce chlorine and chloramine residuals. Again, for the specific example being used to illustrate the method 100, the dechlorination reagent 211 may be a sodium sulfite and the ratio of predetermined weight of dechlorination reagent 211 to inner volume 209 may substantially equal 50 milligrams per liter.

The method proceeds to 110 of FIG. 1, wherein the sample bottles 208 (with the dechlorination reagent 211 disposed inside) are transported to a field site. The field site is remote from the preparation site. For example, the field site may be a public water supply wellfield, an industrial facility, a residential facility, a distribution point in the distribution system of a water district or any site that has a drinking water system flowing through it.

The method proceeds to 112 of FIG. 1, wherein at the field site, water from which a water sample 206 is to be taken, is allowed to flow in order to flush the water system until the water temperature is stabilized. Typically, this will take approximately 3 to 5 minutes.

The method proceeds to 114 of FIG. 1, wherein a sample of water 206 is collected in the sample bottle 208 at the field site that substantially fills the inner volume 209. For example, the sample bottles 208 may be filled to their neck or to a predetermined fill line scribed on the sample bottle. As the water sample 206 is being collected, care must be taken not to flush out the dechlorination reagent 211.

The method proceeds to 116 of FIG. 1, wherein the sample bottles 208 are capped after collecting the water sample 206 and agitated by hand until the dechlorination reagent 211 is dissolved.

The method proceeds to 118 of FIG. 1, wherein the dispenser 200 is operated to substantially dispense the calibrated weight per water sample 205 of microbial inhibitor 202 into the sample of water 206 collected in the sample bottle 208. Again, by way of the specific example being utilized to illustrate the method 100, the reagent dispenser 200 would be held over the sample bottle 208 opening and its triggering mechanism 218 would be pumped twice. Each pump would dispense substantially the calibrated weight per application 204 of 125 mg (e.g., plus 10%) of sodium bisulfate into a 250 ml sample bottle 208 that was filled with the collected water sample 206. The sample bottle 208 would again be capped and then agitated to dissolve the sodium bisulfate into the water sample 206. Accordingly, the concentration of sodium bisulfate to water in the sample bottle would be substantially 1.0 g/L and the pH of the water sample 206 should be reduced to 4 or less. The acidic water substantially prohibits the growth of microbes that could contaminate the sample 206 during transport or storage prior to testing for the 1, 4-dioxane.

The method proceeds to 120 of FIG. 1, wherein the water samples 206 are cooled to maintain their temperatures within a predetermined range of temperatures prior to delivery to a laboratory for analysis. For example, such predetermined range of temperatures may be as follows:
  Samples received at a laboratory during the first 48 hours after collection must not exceed 10 degrees centigrade (C).
  Samples that are not received at the laboratory during the first 48 hours after collection must be maintained at a temperature range of between 1 and 6 degrees C. and shall not arrive at the laboratory at a temperature above 6 degrees C.

The water samples may be cooled by several different well-known methods. For example, they may be packed in ice or refrigerated.

The method proceeds to 122 of FIG. 1, wherein, upon arrival at the laboratory, pH and total chlorine checks are done on all water samples 206 prior to analysis by the laboratory. Examples of such pH and total chlorine tests may be as follows:
  The total chlorine is determined prior to pH determination using any of several well-known methods. Total chlorine must be less than 0.10 mg/L or corrective action must be taken.
  pH is then determined using any of several well-known methods. The pH must be less than 4 or corrective action must be taken.

The method proceeds to 124 of FIG. 1, wherein, after the pH and total chlorine checks are done, the water samples 206 are maintained within a temperature of from 1 to 6 degrees C. prior to analysis.

The method proceeds to 126 of FIG. 1, wherein the water samples 206 may not be held for more than 28 days from the date of collection to the date of extraction. Sample extracts, wherein a water sample 206 goes through a solid-phase extraction process, may be stored at minus 5 degrees C. and protected from light for an additional 28 days before analysis.

The method proceeds to 128 of FIG. 1, wherein the water samples 206 are analyzed for 1, 4-dioxane. Determination of 1, 4-dioxane may be done, for example, by a GC/MS (Gas Chromatograph/Mass Spectrometer) system that meets all QC requirements of the method.

Figure 2:
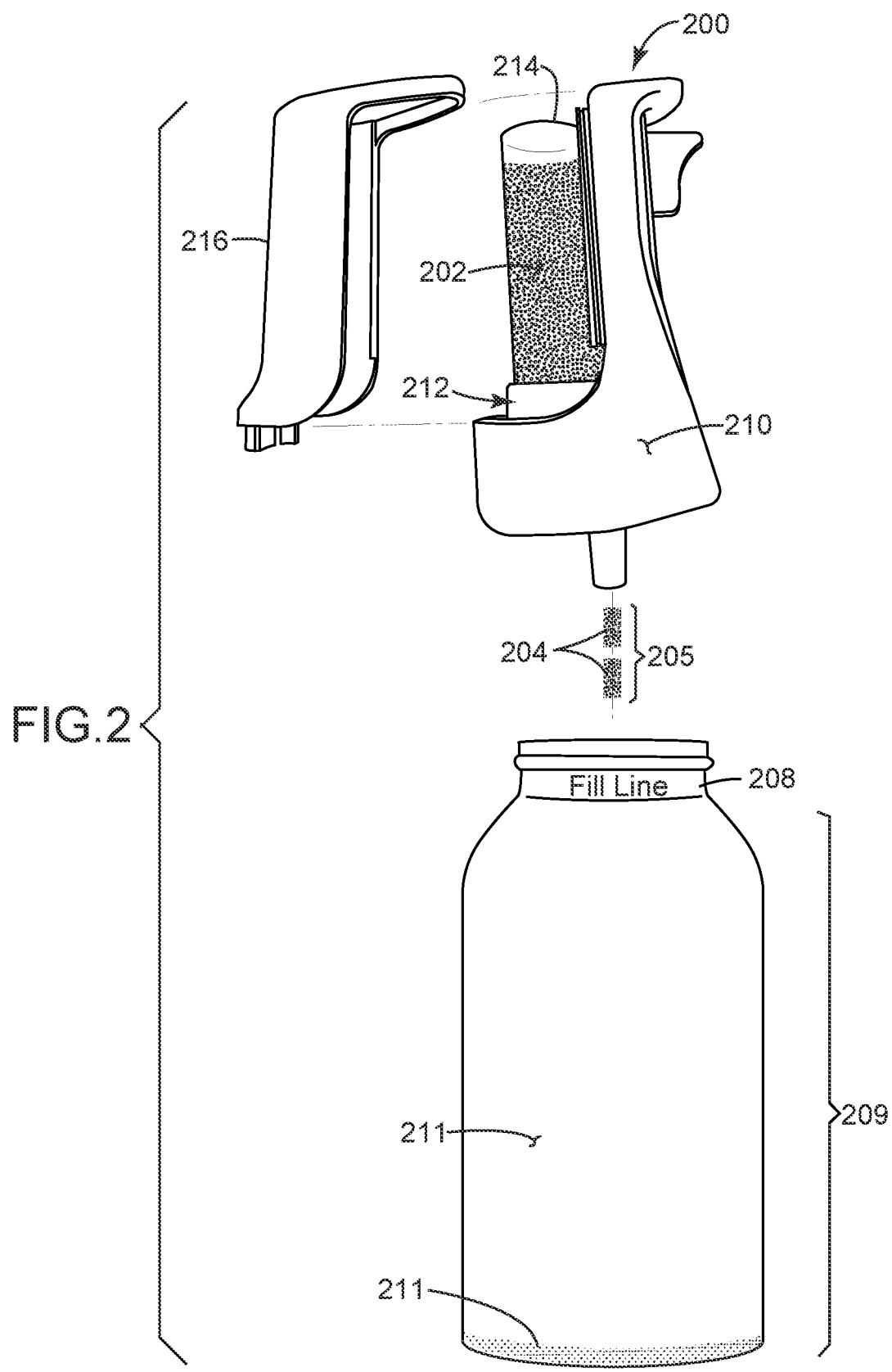
FIG. 2 depicts an example of a perspective view of a calibrated reagent dispenser used in a method of collecting a drinking water sample for determination of 1, 4-dioxane in drinking water according to aspects described herein.

Referring to FIG. 2, an example of a perspective view of a calibrated reagent dispenser 200 used in the method 100 of collecting a drinking water sample 206 for determination of 1, 4-dioxane in drinking water is depicted. The dispenser 200 is operable to dispense a microbial inhibitor 202 in repetitive discrete calibrated weights per application 204 of the dispenser. As such, a total calibrated weight per water sample 205 of the microbial inhibitor 202 (e.g., an integer multiple of the calibrated weight per application 204) may be added reliably and accurately to drinking water samples 206 immediately after the samples 206 have been collected in a sample bottle 208.

An example of a commercial reagent dispenser that may be calibrated and/or modified to dispense a specific microbial inhibitor 202 is a Hach Swiftest™ dispenser having a product number of 2802300 that is made by the Hach Company of Loveland, Colo., USA (herein the Hach dispenser). The Hach dispenser is normally used for chlorine testing in water samples. However, the Hach dispenser may be calibrated and/or modified to enable 1, 4-dioxane testing.

The sample bottle 208 has an inner volume 209 designed to contain substantially that volume 209 of water sample 206 after the sample bottle 208 has been substantially filled with the water sample 206. Additionally, the sample bottle 208 may also contain a dechlorination reagent 211 deposited into the sample bottle 208 at a preparation site. The dechlorination reagent 211 is designed to reduce chlorine and chloramine residuals in the water sample 206 after it has been dissolved into the water sample 206.

The reagent dispenser 200 includes a housing 210 that contains and supports a dispensing system 212. The dispensing system 212 is operable to receive a container 214 of the microbial inhibitor 202. The dispenser 200 also has a cover 216 designed to enclose and protect the dispensing system 212 within the housing 210.

The container 214 may be composed of any appropriate material suitable to contain the microbial inhibitor. For example, the container 214 may be glass, plastic or metal.

Figure 3:
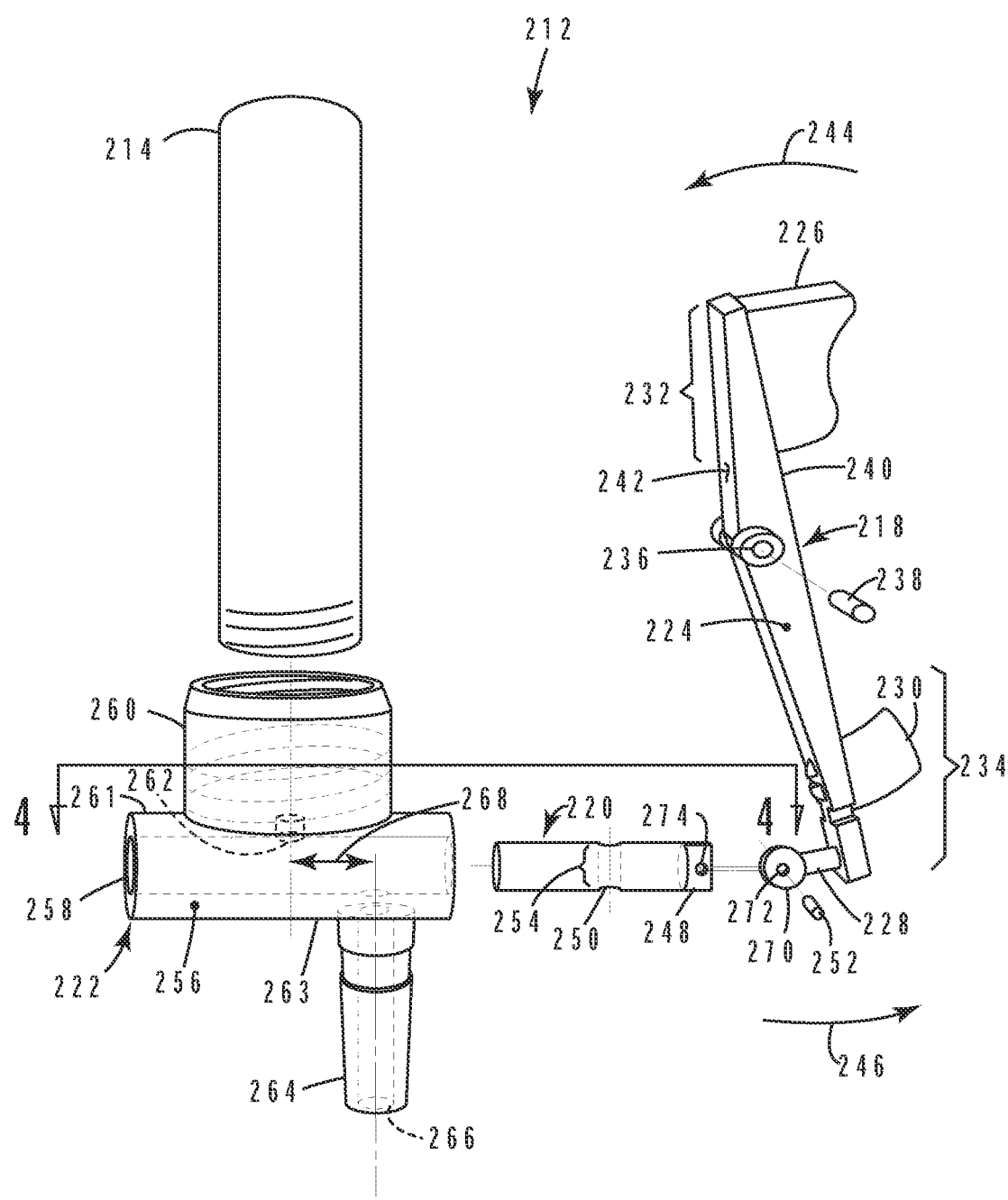
FIG. 3 depicts an example of an exploded perspective view of a dispensing system of the calibrated reagent dispenser of FIG. 2 according to aspects described herein.

Referring to FIG. 3, an example of an exploded perspective view of the dispensing system 212 of dispenser 200 is depicted. The dispensing system 212 includes a triggering mechanism 218, a metering piston 220 and a metering receptacle 222.

The triggering mechanism 218 of dispensing system 212 includes an elongated lever member 224, a trigger 226, a connecting rod 228 and an optional indicating post 230. The lever member 224 has first end portion 232 and an opposing second end portion 234 with a lever through-hole 236 positioned therebetween. The lever through-hole 236 is sized to pivotally attach to a housing post 238 that is an integral part of the housing 210. The housing post 238 provides support for the lever member 224 and acts as a fulcrum upon which the lever member 224 may pivot.

The trigger 226 is positioned on the first end portion 232 and extends laterally from a first side 240 of the lever member 224. The connecting rod 228 is positioned on the second end portion 234 and extends laterally from an opposing second side 242 of the lever member 224. The optional indicating post 230 is positioned on the second end portion 234 and extends laterally from the first side 240 of the lever member 224. As such, when the trigger 226 is moved (or pumped) in a right to left counterclockwise direction (as indicated by arrow 244), the connecting rod 228 and indicating post 230 will move in a left to right counterclockwise direction (as indicated by arrow 246).

The optional indicating post 230 will protrude out of the housing 210 to indicate that the trigger 226 is being pumped and as the triggering mechanism 218 rotates in the counterclockwise direction. The optional indicating post 230 will recess into the housing 210 to indicate that the trigger 226 has been released and as the triggering mechanism rotates in the clockwise direction.

The metering piston 220 of dispensing system 212 includes a connecting tab 248 and a calibrated metering through-hole 250. As will be explained in greater detail herein, the connecting tab 248 is operable to pivotally connect to the connecting rod 228 and be advantageously anchored thereto by a connecting pin 252 that extends entirely through the tab 248 and connecting rod 228 to provide structural strength. Also, as will be explained in greater detail herein, the metering through-hole 250 has a calibrated through-hole volume 254 that is sized to dispense a discrete calibrated weight per application 204 of microbial inhibitor 202 from the dispenser 200.

The metering receptacle 222 of the dispensing system 212 includes a receptacle body 256 having an inner hollow cylindrical core 258 that is sized to slidably receive the metering piston 220. The metering receptacle 222 also includes a engagement port 260 disposed on a top surface 261 of the receptacle body 256, wherein the container port 260 has female threads for engaging with the container 214 of microbial inhibitor 202. The engagement port 260 also includes a first metering passageway 262, which extends from a bottom of the engagement port to the core 258 of the metering receptacle 222.

The metering receptacle 222 also includes a dispensing shaft 264 that is offset from the engagement port 260 and disposed on an opposing lower surface 263 of the body 256 of the metering receptacle 222. The dispensing shaft 264 includes a second metering passageway 266 that extends through the dispensing shaft 264 and into the core 258. The first metering passageway 262 and the second metering passageway 266 are offset by a distance 268 within the core 258.

Figure 4:
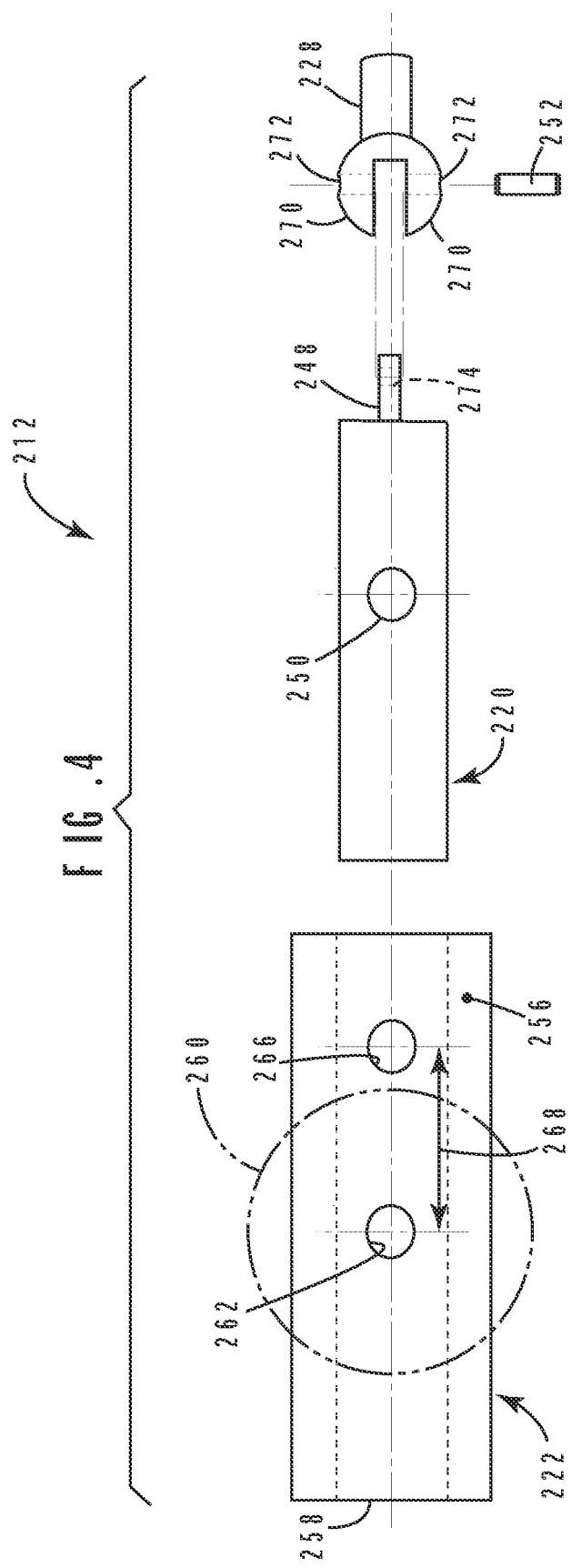
FIG. 4 depicts an example of a top exploded view of the dispensing system of FIG. 3 taken along the line 4-4 according to aspects described herein.

Referring to FIG. 4, an example of a top exploded view of the dispensing system 212 taken along the line 4-4 in depicted. This view is looking down on the body 256 of the metering receptacle 222, the metering piston 222 and the connecting rod 228.

The connecting rod 228 includes a pair of bifurcated branches 270 each with a first pin through-hole 272 extending entirely through. The bifurcated branches are sized to receive and straddle the connecting tab 248 of the metering piston 220 therebetween. A second pin through-hole 274 extends entirely through the connecting tab 248. The second pin through-hole 274 substantially aligns with the first pin through-holes 272 when the tab 248 is engaged with the bifurcated branches 270.

The connecting pin 252 is sized to securely fit entirely through the first pin through-holes 272 of each branch 270 and entirely through the second pin through-hole 274 of the tab 248 to provide enhanced structural strength to the connection between metering piston 220 and connecting rod 228. The pin may be made of any appropriate material for the design application, but is preferably made of a metal, such as steel, tin or iron.

During operation of the triggering mechanism 218, the metering piston 220 will be made to traverse the distance 268 within the core 258 of the metering receptacle 222 such that the metering hole 250 will reciprocate between an alignment with the first metering passageway 262 and an alignment with the second metering passageway 266.

Advantageously, the connecting pin 252 enables the tab 248 of the metering piston 220 to pivotally engage with the branches 270 of the connecting rod 228 when the metering piston 250 is reciprocating within the core 258. Additionally, the connecting pin provides the structural strength required to prevent the connecting rod 228 and metering piston 220 from separating during operation of the dispenser 200.

The connecting rod 228 in this example is illustrated with bifurcated branches 270 that straddle the connecting tab 248 of the metering piston 220. However, one skilled in the art would recognize that the metering piston 230 may include a bifurcated tab that straddles a single end portion of the connecting rod 228. In either case, for proper structural integrity, the connecting pin 252 should extend entirely through both the tab 248 and connecting rod 228.

Figure 5:
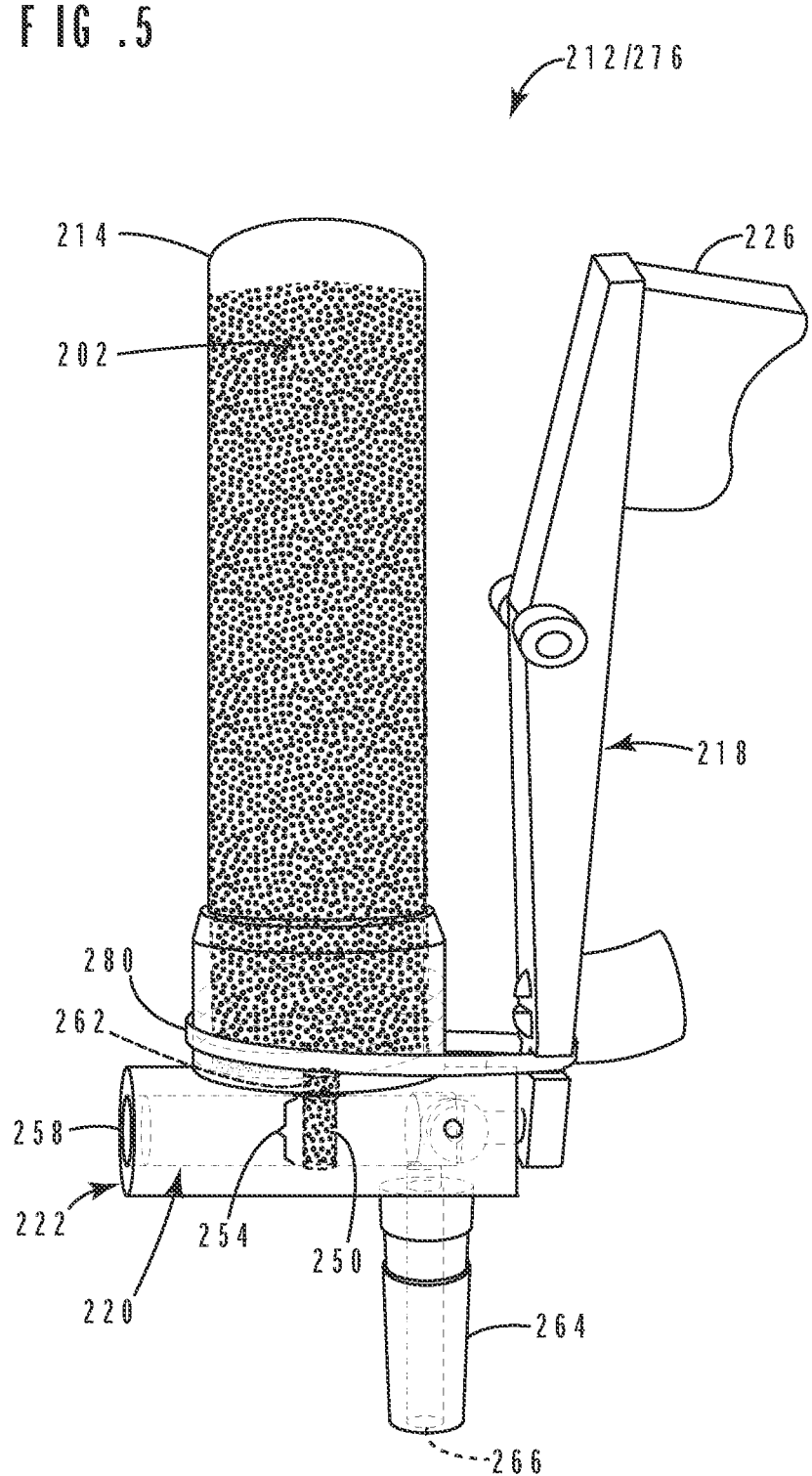
FIG. 5 depicts an example of a perspective view of the dispensing system of FIG. 3 in a non-dispensing first position according to aspects described herein.

Referring to FIG. 5, an example of a perspective view of the dispensing system 212 in a non-dispensing first position 276 is depicted. Also referring to FIG. 6, an example of a perspective view of the dispensing system 212 in a dispensing second position 278 is depicted. During operation, when the trigger 226 is not squeezed, an elastomeric band 280 holds the dispensing system 212 in the non-dispensing first position 276. Additionally, when an operator fully squeezes (e.g., pumps) the trigger 226 than the elastomeric band 280 is stretched and the dispensing system 212 moves to its dispensing second position 278.

Though an elastomeric band 280 is utilized in these examples as the device that holds the dispensing system 212 in the first position, one skilled in the art would recognize that other resilient devices may also be used to do essentially the same thing. For example, a spring may be used rather that an elastomeric band.

Referring more specifically to FIG. 5, during operation, when the dispensing system 212 is in the non-dispensing first position 276, the elastomeric band 280 pulls the triggering mechanism 218 flush against the metering receptacle 222. In this position, the metering hole 250 is aligned with the first metering passageway 262 and microbial inhibitor 202 is allowed to fill the volume 254 of the metering hole 250.

Since the volume 254 of the metering hole 250 determines the weight of microbial inhibitor 202 that will be dispensed per application, then it is important that the volume 254 be sized to receive the calibrated weight per application 204 that is required for any specific microbial inhibitor 202. More specifically the volume of the metering hole 250 must be sized to receive a calibrated weight per application 204 that is an integer multiple of the calibrated weight per water sample 205. The calibrated weight per water sample 205 being such that a ratio of the calibrated weight per water sample 205 to inner volume 209 of the sample bottle 208 substantially equals a predetermined concentration of microbial inhibitor 202 per liter of water determined to acidify water to a pH of 4 or less.

The volume 254 of the metering hole 250 may be sized for a specific microbial inhibitor by any number of well-known methods. For example, the metering hole 250 may be drilled or molded to a certain size.

Additionally, different metering pistons 220 may be sized to fit the same metering receptacle 222, but have different sized metering holes 250 for different microbial inhibitors. Moreover, different metering pistons may be sized to fit the same metering receptacle 222, but have different sized metering holes 250 for different calibrated weights per application 204 for the same microbial inhibitor 202.

Accordingly, by way of our previous example, wherein the microbial inhibitor is sodium bisulfate, the sample bottles 208 have an inner volume of 250 mL and the required calibrated weight per water sample is 250 mg, then the volume 254 of the metering hole 250 may be sized to contain 125 mg of sodium bisulfate. As such, each application of the dispenser 200 will provide 125 mg per pump and it will take an integer multiple of two pumps to apply the calibrated weight per water sample.

Alternatively, the metering hole 250 of the given example may be sized to contain 250 mg of sodium bisulfate. As such, each application of the dispenser 200 will provide 250 mg per pump and it will take an integer multiple of one pump to apply the calibrated weight per water sample.

Figure 6:
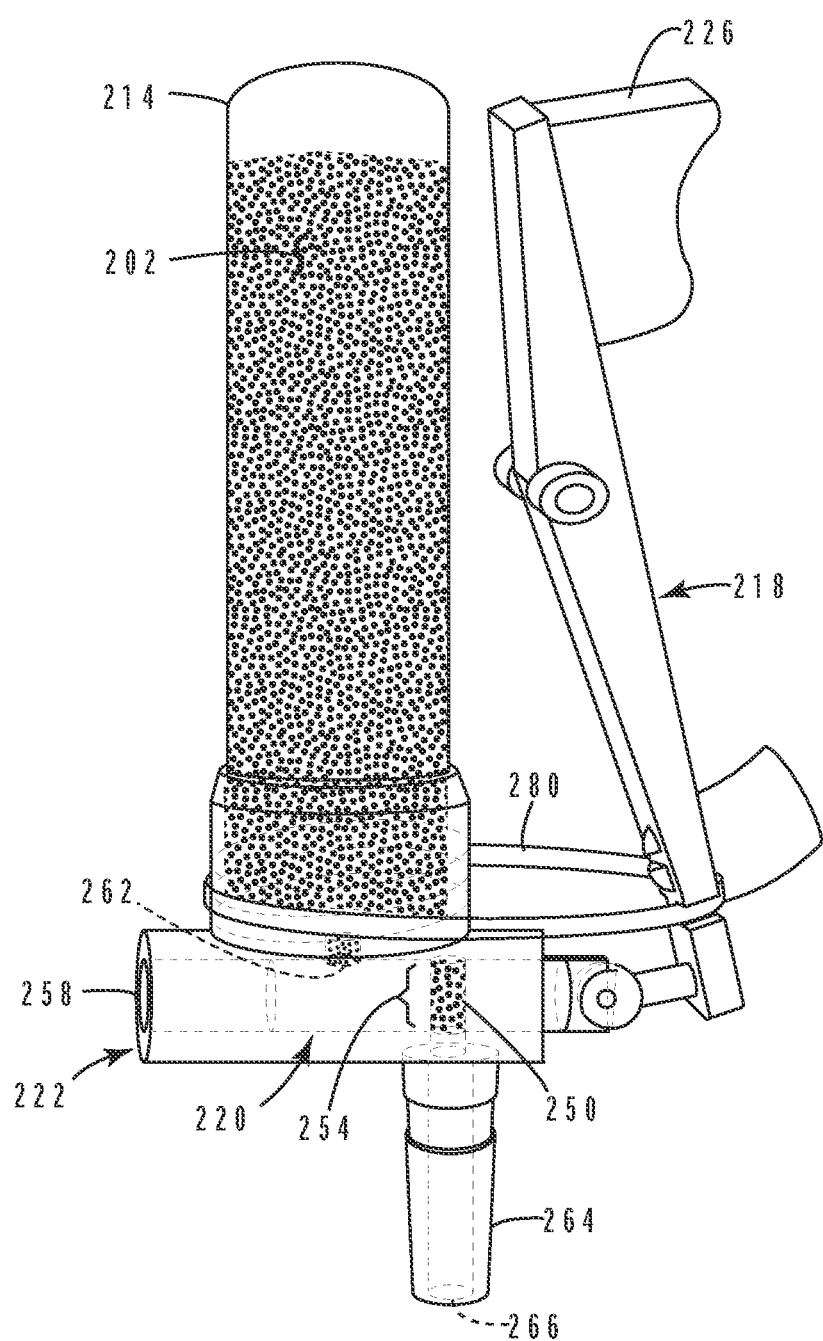
FIG. 6 depicts an example of a perspective view of the dispensing system of FIG. 3 in a dispensing second position according to aspects described herein.

Referring more specifically to FIG. 6, when the dispensing system 212 is in the dispensing second position 278, the trigger 226 is pumped and the triggering mechanism 218 is pivoted away from the metering receptacle 222. In this position, the metering hole 250 is aligned with the second metering passageway 266 and the microbial inhibitor 202 is allowed to dispense freely through the second metering passageway 266 and into a sample bottle 208.

Referring to FIG. 7, an example of a perspective view of a dispenser kit 300 for collecting a sample for determination of 1, 4-dioxane in drinking water is depicted. The dispenser kit 300 includes at least a calibrated dispenser 200 and a container 214 of microbial inhibitor 202. The container 214 may have a removable threaded cap 284 to secure the microbial inhibitor 202 within the container 214 during transport.

More preferably, however, the kit would also include a sample bottle 208 sized to receive an integer multiple number of calibrated weights per application 204 from the calibrated dispenser 200 in order to obtain a required calibrated weight per water sample 205. The sample bottle 208 may have a removable threaded cap 282 to secure the water sample within the sample bottle 208 during transport. Even more preferably, the sample bottle 208 of the kit may also include a predetermined weight of dechlorination reagent 211 in order to reduce chlorine and chloramine residuals.

It should be appreciated that all combinations of the foregoing concepts and additional concepts discussed in greater detail herein (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

Although the invention has been described by reference to specific examples, it should be understood that numerous changes may be made within the spirit and scope of the inventive concepts described. Accordingly, it is intended that the disclosure not be limited to the described examples, but that it have the full scope defined by the language of the following claims.

What is claimed is:

1. A reagent dispenser comprising:
 a housing;
 a container of microbial inhibitor disposed within the housing;
 a dispensing system disposed within the housing and operable to dispense the microbial inhibitor from the container, the dispensing system being calibrated to dispense a calibrated weight per water sample of the microbial inhibitor, such that a ratio of the calibrated weight per water sample to inner volume of a sample bottle substantially equals a predetermined concentration of microbial inhibitor per liter of water determined to acidify water to a pH of 4 or less.

2. The reagent dispenser of claim 1, wherein the dispensing system comprises:
 a triggering mechanism comprising:
  a lever member pivotally connected to a housing of the dispenser,
  a trigger disposed on a first end portion of the lever member, and a connecting rod disposed on a second end portion; and a metering piston pivotally connected to the connecting rod, the metering piston comprising a metering through-hole having a metering through-hole volume sized to receive a calibrated weight per application that is an integer multiple of the calibrated weight per water sample.

3. The reagent dispenser of claim 2, wherein the dispensing system further comprises:

a metering receptacle comprising:

a body having a hollow core sized to receive the metering piston therein;

an engagement port disposed on the body and operable to engage with the container of microbial inhibitor, the engagement port including a first metering passageway extending from a bottom of the engagement port to the core; and a dispensing shaft disposed on the body, the dispensing shaft including a second metering passageway extending through the dispensing shaft to the core, the second metering passageway being offset from the first metering passageway;

wherein, when the dispensing system is in a first position, the metering through-hole of the metering piston is aligned with the first passageway enabling the metering through-hole to receive the calibrated weight per application of microbial inhibitor from the container; and wherein, when the dispensing system is in a second position, the metering through-hole of the metering piston is aligned with the second passageway enabling the calibrated weight per application to be dispensed from the metering through-hole and through the dispensing shaft.

4. The reagent dispenser of claim 2 comprising:

the metering piston including a connecting tab disposed thereon;

the connecting rod including a pair of bifurcated branches, each branch with a first pin through-hole extending entirely through, the bifurcated branches being sized to receive and straddle the connecting tab of the metering piston therebetween;

a second pin through-hole extending entirely through the connecting tab, the second pin through-hole substantially aligning with the first pin through-holes when the connecting tab is straddled by the bifurcated branches; and a connecting pin sized to securely fit entirely through the first pin through-holes of each branch and entirely through the second pin through-hole of the tab to pivotally connect the metering piston to the connecting rod.

5. A kit for collecting a sample for determination of 1,4-dioxane in drinking water, the kit comprising:

a supply of microbial inhibitor; and a reagent dispenser operable to dispense the microbial inhibitor, the dispenser being calibrated to dispense a calibrated weight per water sample of the microbial inhibitor, such that a ratio of the calibrated weight per water sample to inner volume of a sample bottle substantially equals a predetermined concentration of microbial inhibitor per liter of water determined to acidify water to a pH of 4 or less.

6. The kit of claim 5, comprising:

the microbial inhibitor being a sodium bisulfate; and the concentration of microbial inhibitor per liter of water is substantially 1 gram per liter.

7. The kit of claim 6, comprising:

the sample bottle having the inner volume; and a predetermined weight of a dechlorination reagent disposed in the sample bottle such that a ratio of the predetermined weight to the inner volume of the sample bottle substantially equals a predetermined concentration of dechlorination reagent per liter of water determined to reduce chlorine and chloramine residuals.

8. The kit of claim 7, comprising:

the dechlorination reagent being a sodium sulfite; and the concentration of dechlorination reagent per liter of water is substantially 50 milligrams per liter.

9. The kit of claim 5 wherein the calibrated dispenser comprises:

a triggering mechanism comprising:

a lever member pivotally connected to a housing of the dispenser, a trigger disposed on a first end portion of the lever member, and a connecting rod disposed on a second end portion; and a metering piston pivotally connected to the connecting rod, the metering piston comprising:

a metering through-hole having a metering through-hole volume sized to receive a calibrated weight per application that is an integer multiple of the calibrated weight per water sample.

10. The kit of claim 9 wherein the calibrated dispenser comprises:

the metering piston including a connecting tab disposed thereon;

the connecting rod including a pair of bifurcated branches, each branch with a first pin through-hole extending entirely through, the bifurcated branches being sized to receive and straddle the connecting tab of the metering piston therebetween;

a second pin through-hole extending entirely through the connecting tab, the second pin through-hole substantially aligning with the first pin through-holes when the connecting tab is straddled by the bifurcated branches; and a connecting pin sized to securely fit entirely through the first pin through-holes of each branch and entirely through the second pin through-hole of the tab to pivotally connect the metering piston to the connecting rod.

* * * * *